United States Patent [19]

Derechinsky et al.

[11] Patent Number: 4,583,537
[45] Date of Patent: Apr. 22, 1986

[54] CONVERGENT MULTIBEAM UNIT FOR RADIATION

[76] Inventors: Victor E. Derechinsky; Osvaldo O. Betti, both of Sarmiento 2172, Buenos Aires, Argentina, 1044

[21] Appl. No.: 441,595

[22] Filed: Nov. 12, 1982

[30] Foreign Application Priority Data

Nov. 18, 1981 [AR] Argentina .............................. 287500

[51] Int. Cl.$^4$ .............................................. A61B 6/00
[52] U.S. Cl. ..................................... 128/303 B; 128/65
[58] Field of Search ..................... 128/303 B, 653, 659; 378/64, 65, 17, 20, 208, 209

[56] References Cited

U.S. PATENT DOCUMENTS

| | | | |
|---|---|---|---|
| 2,901,302 | 8/1959 | Kizaur | 378/209 X |
| 3,506,826 | 4/1970 | Kosters | 378/209 X |
| 3,585,386 | 6/1971 | Horton | 378/208 |
| 3,627,250 | 12/1971 | Pegrum | 378/65 X |
| 4,223,227 | 9/1980 | Horwitz | 378/65 X |
| 4,360,028 | 11/1982 | Barbier et al. | 128/303 B X |

FOREIGN PATENT DOCUMENTS 2724321 12/1977 Fed. Rep. of Germany ... 128/303 B

Primary Examiner—Edward M. Coven
Attorney, Agent, or Firm—Berman, Aisenberg & Platt

[57] ABSTRACT

A convergent multibeam unit for radiation is disclosed. The unit comprises a lineal accelerator as a radiation means which is angularly displaceable around a virtual axis which intersects the radiation axis of same, said lineal accelerator being combined with a stereotaxic device constituting a frame angularly displaceable around an axis which is substantially normal to the axis of angular displacement of the lineal accelerator and contains the isocenter of same; the angular displacement arches of the radiation axis of said lineal accelerator and of said stereotaxic frame defining a virtual spherical cap in the center of which and coinciding with said isocenter, there is located the area to be radiated on said virtual spherical cap which determines multiple radiation entries converging on said area.

11 Claims, 4 Drawing Figures

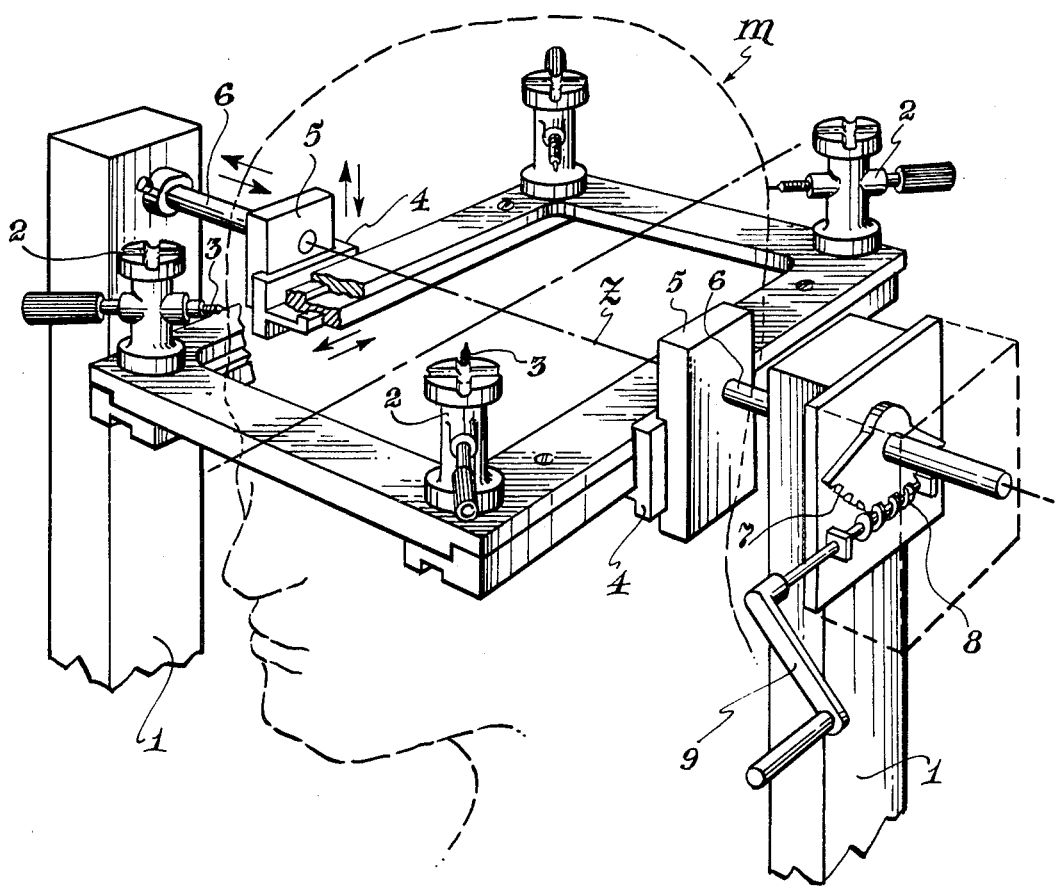

CONVERGENT MULTIBEAM UNIT FOR RADIATION

BACKGROUND OF THE INVENTION

The present invention refers to a convergent multibeam unit for radiation and particularly to a combination of lineal accelerator with stereotaxic means that contribute with substantial advantages to the devices used at present for radiation of the cerebral structures.

Stereotaxy, which was initiated at beginning of this century with a Horsley and Clark device used on animals for experimentation, made it possible to locate different intracerebral structures with precision and to reach said structures with stimulation and coagulation electrodes; it was developed until 1947, when Spiegel and Wycis reported in the U.S.A. the first concept of a stereotaxic device adapted for human use. Subsequently, different reports were made from scientific societies of several European countries.

In France, Prof. Jean Talairach was the pioneer of this discipline; his contribution constitutes the most important neurosurgical work of that country.

At present the possibility of observing the course of the encephalic vessels in each individual case makes it possible to locate the cerebral fissures and convolutions with precision, and consequently, effect multiple biopsies. From an exact diagnosis and the consequent histoprognosis an adequate therapy can be selected.

The possibilities of treatment would be:
(a) Surgical ablation (total or partial) if a situation and extent of injury allows it,
(b) Radioactive interstitial implantation (with Iridium 192 or Iodine 125),
(c) External radiation with lineal accelerator due to its penetration and minor effect on the skin compared, for example, with Cobalt 60,
(d) Radiation with Cobalt 60 with multiple fixed sources ("Gamma Unit"), to which reference shall be made below and, finally;
(e) Radiation with the convergent multibeam unit of the invention in stereotaxic condition.

Of the radiation methods in which we are interested, implantation is effected on small glia tumors of low malignant degree and situated in the nervous parenchyma.

Radiation through teletherapy with a lineal accelerator is used only on extensive tumors, or in protocols of "implantation-teletherapy with lineal accelerator" association, placing an important tumoricide dose on the tumor itself and a smaller dose on the periphery of same to destroy the tumor cells that are at a distance from the center of the injury and that can be responsible for its reappearance.

The application of the convergent multibeam unit of the invention is based on the necessity to apply a high dose in the center of the tumor, with a rapid decrease of the dose on the edges and the possibility of protecting the normal operational structures that have not been infiltrated by a tumor, without applying too small a dose on the latter.

Numerous working trials have demonstrated that, as the volume of radiation is increased, either through teletherapy or interstitial, the possibilities of radionecrosis are consequently increased. This means the death of the tumor in a significant of cases, but the complications to which this leads also cause the death of the patient. Over and above a volume of approximately $5 \times 5 \times 5$ cm a radionecrosis is mortal notwithstanding its surgical extirpation (which is sometimes possible), due to complications of uncontrollable edema. Experience with biopsies and necropsies corroborates this.

If at the same time the precision of the methodology permits examination of the exact limits of the injury, the ideal would be to apply a therapy that, without losing its efficiency, must be as circumscribed as possible, reducing its diameter. This implies the necessity of a strict localization, obtainable by means of estereotaxy and a minimum of the complications based on the reduction of the diameter of the radiation beams and the multiplication in number of the entries that allow to obtain, within the perfectly admissible tolerances for each of them, the concentration on the area, in this case the tumor, of the sum of said radiations.

The focal concentration of numberless radiation beams of high energy (6 to 12 MV) centered on the injury obtain the desired end.

The smallest fields used in teletherapy for the axion are of $4 \times 4$ cm. If, as stated above, radionecrosis is the inevitable result of radiation on volumes of the order of $5 \times 5 \times 5$ cm, the danger limits become very narrow.

SUMMARY OF THE INVENTION

The convergent multibeam unit for lineal accelerator of the invention is particularly applicable in small injuries, although those of medium size diameter can be treated by more than one application separated in different periods. A particular quality of those treatments is that they can be effected in one only session, which substantially modifies the classical concepts of radiotherapy.

In view that they also radiate small volumes, the dose can be increased, which also causes very special changes in the tumor structure, such as the transformation of solid tumors, or hypodense into radionecrotic hyperdense tumors that, due to their small volume can be removed or that the reduction of the volume improves the symptomatology.

This modification of the tumor structure also opens new ways in the interpretation and treatment of tumors, whether glia tumors or acoustic neurinoma in hypophysis adenoma and craniopharyngioma, among others.

On the other hand, vascular injuries, such as angiomas, aneurisms and even cavernous-carotid fistula, have been treated with said concentrated radiations in one session with the result of the progressive obliteration of the defective afferent vessels or of aneurism collum, as the answer to a vasculities by endotelities by radiation. This subject by itself is sufficient to justify this technology that gives new solutions to complex problems in vascular radiosurgery.

As a complement of the foregoing may be added the therapeutic radioinjuries with the object to cause the exclusion of structures of pathological performance within different operating cerebral circuits, that originates the restructuring of same with the disappearance of clinical symptoms such as certain Parkinson symptoms, obsessive neurosis and pains caused by cancer.

With the object to obtain multiple entries for radiation, investigators of the Karolinska Hospital in Sweden, after working at the University of Upsala with different high energy radiation systems, arrived at a solution that allowed them to use a high energy equipment within the hospital premises. Thus, the group directed by Professor Lars Leksell designed mechanically complex equipment using Cobalt 60 as the radiation source.

This device, known as "Gamma Unit", already mentioned above, has a head in the shape of a spherical can at present with 200 sources of Co 60, radially directed toward a center that can be given a high dose of radiation. The periphery of said radiated volume receives a small dose of radiation due to the multiplication of the entries.

This solution presents some difficulties, especially due to the complexity of the apparatus, the high cost and restricted scope of application of which makes its service possibility very limited. Added to the foregoing is the natural decrease of the dose to half the initial energy in a period of five years, that requires the replacement of the sources. Furthermore, the energy of Co 60 varies from 1.17 to 1.33 MV, which is lower than that obtained with a lineal accelerator that varies from 6 to 18 MV. On the other hand, the fact of having fixed multiple entries confines the possibility of its use and thus, enormously increases costs and in the economic aspect restricts the possibilities of treatment.

Searching for an adequate solution of those problems, the conclusion was arrived at that means should be found that are capable of radiating high energy and which, having an ample scope of application, could be used in a combination where the stereotaxic techniques could be used.

A lineal accelerator is a high energy radiation system that has other applications besides those of neurosurgery as, among other purposes, it is already used for radiotherapy treatment. Which means that, as a source of radiation, its scope of application is very ample. The energy of the photons of said accelerator varies from 6 to 18 MV that, as mentioned above, is much higher than that of Cobalt 60.

The combination to obtain the multibeam unit of the invention thus obtains a device that having higher radiation energy, allows a greater scope of application. To the foregoing must also be added that the flow of photons per sq. mm. is 1000 times higher than that of Cobalt 60. Besides, having a variable multiplicity of entries within the innumerable possible entries on a virtual spherical cap defined by the combined sweeping arches of the lineal accelerator with the stereotaxic device, provides this method with a higher flexibility.

Therefore, the multibeam unit of the invention was conceived based on a stereo-tele-radiotherapy system that has the desired characteristics as well as substantial advantages over the systems known at present.

The assembly includes:

Modification and adaptation of the stereotaxic system to transform it into an arch system.

Adequate collimation system of 10 MV photons beam (that correspond to the lineal accelerator selected in combination with said system) to obtain a geometry with minimum penumbra.

System to hold the body of the patient, adaptable to all the positions of the head that does not burden the supports of the stereotaxic system and that maintains with same a common rotation axis.

In said device the approaching system by means of grates which is used with stereotaxic frames has been eliminated in view that, although it is useful for certain purposes, it does not have the particular characteristics obtained with the invention in which as great a multiplicity of entries as desired is obtained due to the fact that the scope of possibilities is provided by means of continuous combined runs of the accelerator and the stereotaxic frame and with same, the head of the patient.

The transformed stereotaxic frame has the characteristic that the center of the injury in the brain that is fixed by the cranium to said frame becomes the isocenter of an axis system that allows said frame to effect an anterior-posterior angular displacement so as to allow the approach on all its useful surface.

The frame can go up or down so that the center of the injury can be situated on the rotation axis, being connected to the retention system by means of slides. Said rotation axis, assembled on bushings arranged on each side of the frame retention system, is aligned so that its central axis can coincide with the center of the injury to be treated. As the injury can be situated in the center line or be displaced to one side of said center line, the system allows lateral displacements of up to 7 cm. to both sides.

The device allows placing the injury in the isocenter of the system that also coincides with the rotatory displacement isocenter of the lineal accelerator with which same is combined.

The assembly maintains the coincidence of both isocenters for which purpose the support of the stereotaxic frame has a rigid and non-deformable base with columns that do not admit any kind of bending under the conditions to which the unit is submitted and with a register system that allows the above mentioned coincidence of both isocenters.

As the opening of the quadrangular collimation of the lineal accelerator is prepared for areas the smallest of which generally used are of 3×3 cm., and it is desired to work with a beam in which the dose on the periphery is 1% lower than that of the dose in the axis of the beam, and in order that said reduction should occur within 5 mm from the axis of the beam, it is necessary to add a supplementary collimation to the accelerator, interposed in a stretch of 2×2 cm. of said accelerator.

The attached secondary collimator has a diameter of 5 cm. and a cylindrical orifice with a diameter of 3, 5, 9 and 12 mm. and 15 cm. long. Its distal end is situated at 12,5 cm. from the isocenter of the lineal accelerator.

The multiplication of the entries obtained with this unit which, as stated above, constitutes one of its principal advantages, has the object to obtain the maximum reduction of the radiation that must pass through the normal structures to reach the area to be treated. A maximum of between 30 and 50 rads per entry has been imposed, said figure being lower than the 200 rads adopted as the maximum by Leksell in his above mentioned system ("Gamma Unit"), supplied with 200 sources of Co. 60.

The intercrossed radiation beams in the scope of the frontal bone due to the rotation of the accelerator, and in the sagittal flat due to the rotation of the stereotaxic assembly combined with the accelerator, said rotations defining a virtual spherical cap, produce the effect of "crossed fires" that determine a small volume within which radiation will be at the maximum, the center of said volume being occupied by the area to be radiated.

In the periphery of said volume and due to the above mentioned multiplicity of entries, that can be selected from the 1225 possible entries if angular displacements of 5° are effected over a virtual spherical cap in sweeping arches in the order of 175° (if arches of 180° are taken, the radiation at the ends will be much higher than that foreseen); or of the 28,900 possible entries if the angular displacements of the lineal accelerator and the stereotaxic assembly are of 1° at a time on sweeping arches of 170°; radiation rapidly decreases to less than 1% of the central dose, which allows an excellent tissular tolerance and thus constitutes one of the most important advantages of the invention.

One of the characteristics of the combination of the stereotaxic assembly with the lineal accelerator is the support system of said assembly whose base is unmovably associated with the base of the accelerator, and in which the body of the patient does not mean a load on the supports of the stereotaxic system. It must be taken into account that the unit, besides fulfilling certain precision requirements, must also offer comfortable conditions for a treatment that can last from half an hour to an hour and a half per session.

As to each of the successive positions of the stereotaxic device on the sagittal rotation axis corresponds a series of consecutive positions of the lineal accelerator on the frontal bone, which define the virtual spherical cap that covers the cranial cavity, the body of the patient must accompany the different positions of the head in order to avoid pains or contractures at the cervical area level which must act as compensator of the movements of the head.

This objective was obtained by means of a particular concept of the adaptation means for the patient under treatment, based on a seat with a back, means to regulate the position and height, that is also displaceable on curvilinear guides whose curve center coincides with the isocenter of the system.

Other advantages and characteristics of the invention may be observed from the specifications that for a better understanding and comprehension have several figures attached, which represent the convergent multibeam unit for radiation of the invention in one of its preferred embodiments, as a non-restrictive example of its scope, in which:

BRIEF DESCRIPTION OF THE DRAWINGS

FIG. 4 is a partial view showing details of the stereotaxic device which, combined with a lineal accelerator, integrates the assembly.

DETAILED DESCRIPTION OF THE DRAWINGS

Figure 1:
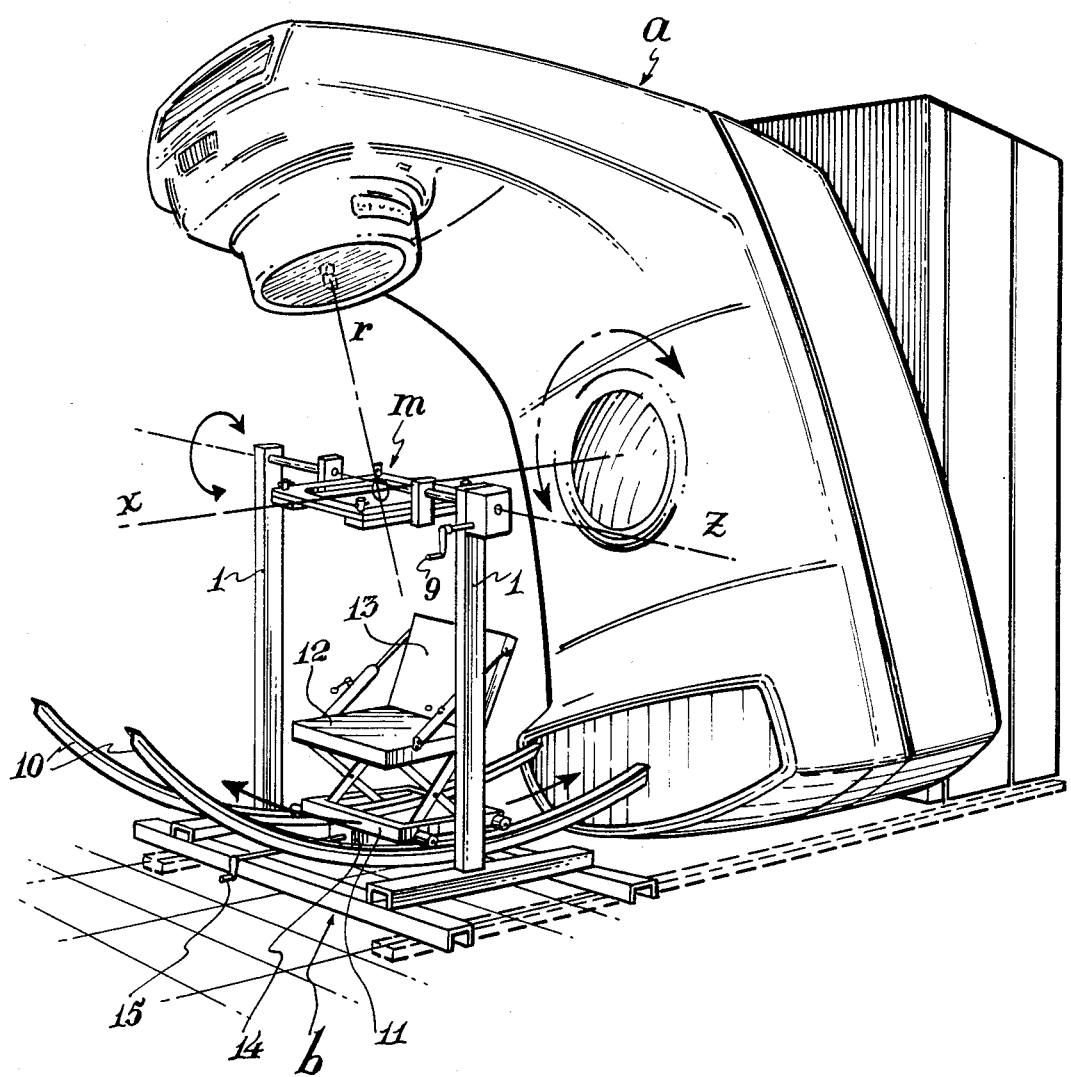
FIG. 1 is a general perspective view of the convergent multibeam unit assembly in which the component parts of same and their combination may be observed.

In the different figures the same reference numbers indicate equal or corresponding parts, the different pieces and/or assemblies are indicated with letters.

As may be observed from the drawings, the convergent multibeam unit for radiation of the invention comprises a radiation means constituted by a lineal accelerator a combined with a stereotaxic assembly mounted on a base b, rigidly associated to the base of said lineal accelerator a, obtaining a convergent radiation system, of multiple entries, that has the characteristics and advantages mentioned above.

Said lineal accelerator a is angularly displaceable around an axis x and has a radiation axis r, the intersection of which defines the isocenter of said accelerator, said isocenter constituting the imaginary and fixed point in space that, whatever is the angular position of the accelerator around the above mentioned axis x, said axis x is intersected with the radiation axis r.

The substantially rigid base of the stereotaxic assembly b is associated, preferably beneath floor level, with the base of accelerator a, thus constituting an assembly without any possibility of the relative displacement of its components. On said base b, a set of rigid columns 1 are placed that form the supports of the stereotaxic frame m (FIG. 4).

Said frame m, supplied with towers 2 with means 3 for fixing to the cranium of the patient, has pieces 4 on the opposite sides, with respect to which it is longitudinally displaceable and fixed by means of bolts to the desired position, that are also displaceable in the normal direction of the former, in respective pieces 5 that have orifices for fixing to the bar gudgeons 6 that define axis z of angular displacement of frame m. The operation of said angular displacement is effected by means of a mechanism with toothed sector 7 that connects with a band 8 operated with handle 9, as shown in FIG. 4.

For placing said frame m, that is fixed to the cranium of the patient, same has the possibility of movement pointed out with arrows in FIG. 4. The lateral displacements of frame m are regulated by the axial displacement of the bar gudgeons 6 into the top orifices of columns 1 which they pass through.

The fixing into position of axis z must be sufficient to contain the isocenter of the lineal accelerator, that is to say, the angular displacement axis x of the lineal accelerator z of the stereotaxic frame m and the radiation axis r are intersected in said isocenter that in the operative condition of the unit, shall correspond to the position of the area to be radiated.

The axial displacement of the bar gudgeons 6 at the top ends of columns 1 allow the lateral displacement of frame m and carry the area, that can be to one side, to the isocenter of the system.

The base b of the stereotaxic assembly has a fixed strip formed by a set of curvilinear rails 10 on which the base 11 is displaced along with a seat 12 that has a back 13.

Figure 2:
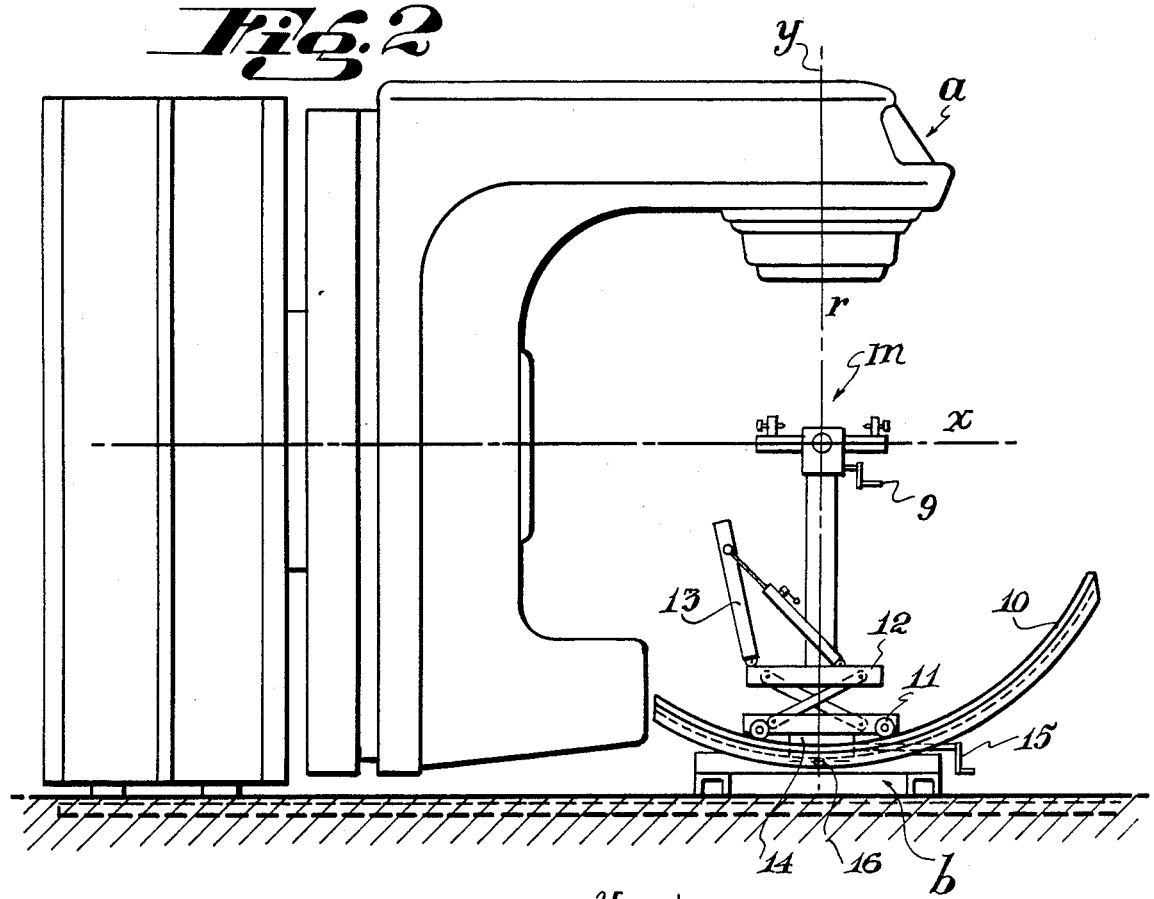
FIG. 2 is an elevated side view that also shows the unit assembly.
Figure 3:
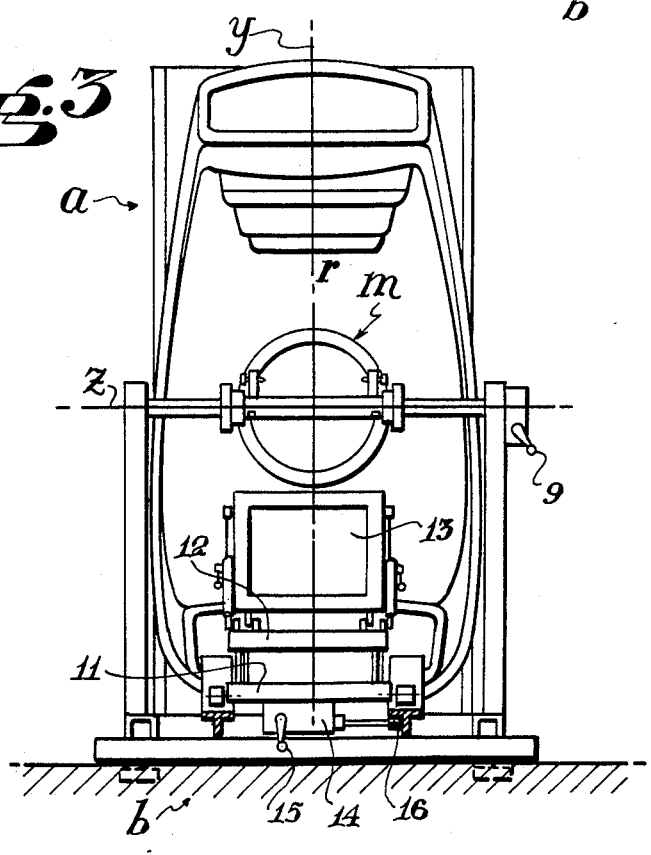
FIG. 3 is a front elevated view and, finally.

Said seat 12, as well as the back 13, have position and height regulation means. The base 11 has a reducing box 14, an operating handle 15 and said box 14 is also connected to a rack rail placed on at least one of the internal sides of one of the curvilinear rails 10, as shown in FIGS. 1 to 3.

The center of curvature of the above mentioned rails 10 coincides with the position of axis z that contains the isocenter of the system, so that with the angular displacement of frame m (with the patient's head) around said axis z, the seat 12 and back 13 assembly that holds the patient is also displaceable around said axis, accompanying the rotation of the above mentioned frame m.

As may be observed from the foregoing description and drawings it is possible to carry out multiple convergent entries on an area to be radiated which, as stated above, is placed in the isocenter of the system, with the combined movement of the arch of the lineal accelerator a on its rotation axis x and the stereotaxic frame m around its axis z, both rotations defining a virtual spherical cap that thus admits multiple entries with the known advantages mentioned above.

As a variation of the invention, the possibility of the rotation frame m around axis z can be replaced by the rotation of same—with the patient—on a vertical axis and (FIGS. 2 and 3) therefore the virtual spherical cap is defined by the angular displacement arch of frame m around axis y and that of the lineal accelerator a around axis x.

On both sweeping arches the desired number of multiple radiation entries may be selected, said radiation, as mentioned above, being concentrated on the small volume around the isocenter of the system in which the area to be radiated is placed.

Having thus particularly described and determined the nature of the invention and the manner in which the same can be put into practice, we hereby declare that the principal object of the same and the different embodiments of same are defined, as regards its scope and claims of exclusive property and right, in the claims that form an inseparable part of the present specifications, which read as follows:

We claim as our invention:

1. A radiation treatment apparatus comprising radiation means for directing treatment radiation along a first axis, said radiation means being mounted for rotation about a second axis which intersects said first axis at an isocenter whereby said radiation passes through said isocenter for all orientations of said radiation means about said second axis, and stereotaxic means for holding an object to be treated, said stereotaxic means comprising seat means for supporting the weight of an object and frame means closely adjacent said isocenter, said frame means being mounted for movement in three orthogonal directions and for rotation about a third axis which intersects said first and second axes at said isocenter, said seat means also being mounted for rotation about said third axis, whereby said radiation will irradiate the portion of said object at said isocenter for any orientation of said stereotaxic means about said third axis.

2. Apparatus according to claim 1 wherein said second axis is horizontal and said third axis is horizontal.

3. Apparatus according to claim 1 wherein said second axis is horizontal and said third axis is vertical.

4. Apparatus as claimed in claim 1 wherein said stereotaxic frame comprises displacement means for regulating the position of said object with respect to said isocenter; said frame being mounted on a set of support columns secured to a base said third axis of said stereotaxic frame being defined by bar means mounted on said columns said stereotaxic means further comprising curvilinear guide means for supporting a displaceable said seat means, the centers of curvature of said guide means coinciding with said third axis.

5. Apparatus according to claim 4 wherein said second axis horizontal and said third axis is horizontal.

6. Apparatus as claimed in claim 4, wherein the stereotaxic frame is laterally mounted on a set of members on which it is longitudinally slidable, said members being also displaceable in a direction transverse to said third axis and being mounted on pieces fixed at the end of said bars, said bars also being adjustable with respect to the support colums; said frame thus having the possibility of a tridimensional displacement capable of placing the position of the area to be radiated in coincidence with said isoncenter.

7. Apparatus as claimed in claim 6, wherein both the stereotaxic frame and the displacement seat have control means for providing mechanically operated displacements.

8. Apparatus as claimed in claim 4, wherein both the stereotaxic frame and the displaceable seat have control means for controlling mechanically operated displacements.

9. Apparatus as claimed in claim 1 further comprising control means for controling displacement of both the stereotaxic frame and the displaceable seat.

10. Apparatus as claimed in claim 1 wherein said stereotaxic frame is mounted on a set of members on which it is longitudinally slidable, said member being also displaceable in a direction transverse to said third axis and being mounted on pieces fixed at the end of said bar means, said bar means also being ajustable with respect to the support colums in the direction of said third axis; whereby said frame has the possibility of a tridimensional displacement capable of placing an area to be radiated in coincidence with said isocenter.

11. Apparatus as claimed in claim 10, wherein both the stereotaxic frame and the displacement seat have control means for providing mechanically operated displacements.

* * * * *